United States Patent [19]

Derroitte et al.

[11] 4,144,390

[45] Mar. 13, 1979

[54] PROCESS FOR THE POLYMERIZATION OF OLEFINS AND CATALYSTS THEREFOR

[75] Inventors: Jean-Louis Derroitte; André Delbouille, both of Brussels, Belgium

[73] Assignee: Solvay & Cie, Brussels, Belgium

[21] Appl. No.: 185,881

[22] Filed: Oct. 1, 1971

[30] Foreign Application Priority Data

Oct. 6, 1970 [LU] Luxembourg .......................... 61816

[51] Int. Cl.[2] .......................... C08F 4/02; C08F 10/02

[52] U.S. Cl. ................................ 526/125; 252/429 R; 252/429 B; 252/429 C; 526/114; 526/115; 526/122; 526/124; 526/352

[58] Field of Search .......... 252/429 C, 429 B, 429 R; 260/88.2, 93.7, 94.9 C, 94.9 DA; 526/124, 125

[56] References Cited

U.S. PATENT DOCUMENTS

| | | | |
|---|---|---|---|
| 3,268,290 | 8/1966 | Gaska et al. | 423/163 |
| 3,644,318 | 2/1972 | Diedrich et al. | 260/94.9 DA |
| 3,676,415 | 7/1972 | Diedrich et al. | 260/94.9 DA |

FOREIGN PATENT DOCUMENTS

| | | | |
|---|---|---|---|
| 75394 | 8/1970 | German Democratic Rep. | 260/94.9 DA |
| 1958488 | 5/1970 | Fed. Rep. of Germany | 260/94.9 DA |
| 7000094 | 7/1970 | Netherlands | 260/94.9 DA |
| 1140649 | 1/1969 | United Kingdom | 260/94.9 DA |

OTHER PUBLICATIONS

Khristov et al., Chemical Abstracts, vol. 61, col. 9161c, Oct. 1964.

*Primary Examiner*—Edward J. Smith
*Attorney, Agent, or Firm*—Pennie & Edmonds

[57] ABSTRACT

This invention relates to the polymerization of α-olefins and to catalysts and cocatalysts for that purpose wherein the polymerization is carried out in the presence of a catalyst comprising an organometallic compound of a metal of Groups Ia, IIa, IIb, IIIa, and IVa of the Periodic Table and a solid cocatalyst comprising the reaction product of a halogenating agent, an organic oxygenated compound of a divalent metal, and a derivative of a transition metal of Groups IVb, Vb, and VIb of the Periodic Table, the proportions of halogenating agent and organic oxygenated compound being that required to result in a reaction product thereof having an atomic ratio of halogen/divalent metal greater than 1. The invention also comprises the method of making the cocatalysts.

4 Claims, No Drawings

PROCESS FOR THE POLYMERIZATION OF OLEFINS AND CATALYSTS THEREFOR

BACKGROUND OF THE INVENTION

In French Pat. No. 1,582,543 in the name of the applicants, there is a description of catalysts for the polymerization of olefins comprising a catalytic solid obtained by reacting a halogenating agent and a derivative of a transition metal with a solid support consisting of an oxygenated compound of a divalent metal in the anhydrous state and low in hydroxyl groups. The oxygenous compounds preferably used are oxides. The reaction conditions of the solid support with the halogenating agent are selected in such a way as to fix such a quantity of halogen that the atomic ratio of halogen to divalent metal is less than 1. While satisfactory, such catalysts are not as active as desired.

SUMMARY OF THE INVENTION

It has now been found that it is possible to prepare much more active catalysts if special solid supports and halogenating agents are used and if the halogenation reaction is carried out under conditions such that the halogen/divalent metal ratio is greater than 1.

The present invention relates to a process for the polymerization and copolymerization of $\alpha$-olefins, particularly ethylene, in which the operation is carried out in the presence of a catalyst comprising an organometallic compound of a metal of groups Ia, IIa, IIb IIIa and IVa of the Periodic Table and a cocatalyst obtained by reacting an organic oxygenated compound of a divalent metal with a halogenating agent selected among chlorinating, brominating and iodinating agents and a derivative of a metal of Groups IVb, Vb and VIb of the Periodic Table, the atomic ratio of halogen to divalent metal of the activated solid support formed by the reaction between the oxygenated compound of a divalent metal and the halogenating agent is greater than 1. The invention also comprises the catalyst products and methods of making them as hereinafter described.

DETAILED DESCRIPTION

In the present invention the oxygenated organic compounds of divalent metal form the solid support and are considered as being organic compounds when their molecules possess divalent metal/oxygen/carbon bonds. Although all organic oxygenated compounds of divalent metals are suitable, it is preferred to use those of magnesium, calcium, zinc, manganese, iron, nickel, cobalt and tin; the best results are obtained with those of magnesium.

The organic oxygenated compound can also be of any desired nature. However, it is preferred to use compounds in which a carbon-containing radical is attached to the divalent metal via the oxygen, which radical contains from 1 to 20 carbon atoms and more particularly from 1 to 6 carbon atoms. These radicals may be saturated or unsaturated, with branched chains, with straight chains or cyclic; they may also be substituted. They are selected in particular from among the alkyl, alkenyl, aryl, cycloalkyl, arylalkyl, alkylaryl, acyl, aroyl radicals and their substituted derivatives.

Examples of organic oxygenated compounds of divalent metals which are suitable for the process of the invention are:

alkoxides such as methanolates, ethanolates, isobutylates, cyclohexanolates and derivatives of benzyl alcohol phenates such as cresolates enolates such as acetylacetonates the salts of carboxylic acids such as acetates, butanoates, laurates, pivalates, crotonates, phenyl acetates, benzoates, malonates, adipates, sebacates, phthalates, mellitates, acrylates, oleates and maleates.

Also suitable are the oxygenated organic compounds of divalent metals having other radicals attached to the magnesium in addition to the carbonaceous radicals attached via the oxygen. Among these other radicals one may mention halide radicals, the hydroxide radicals and radicals derived from inorganic acids such as sulphate, nitrate, phosphate or carbonate radicals.

All these organic oxygenated compounds may be prepared by any known methods, as the reaction between the divalent metal, its oxides or hydroxides, and the corresponding alcohol, phenol, carboxylic acid. They are generally solid and their particle size is not critical. For reasons of convenience, however, it is preferred to use particles whose mean diameter is between 1 to 500 microns and preferably between 40 and 200 microns.

The halogenating agents which are used within the framework of the present invention are chlorinating, brominating and iodinating agents. While all such known agents can be used, those particularly suitable are:

the halogens in the elementary state: $Cl_2$ and $Br_2$ and the like;

hydrogen halides: HCl, Hbr and HI, and the like;

oxyhalides of non-metals: $So_2Cl_2$, $SOCl_2$, NOCl, $COCl_2$ and $POCl_3$ and the like;

halides of non-metals: $PCl_3$ and $PCl_5$ and the like; halogenomethanes: chloromethanes halides of metals and ammonium: $AlCl_3$ and $NH_4Cl$ and the like.

Of all the halogenating agents, it is preferred to use chlorinating agents.

The reaction with the halogenating agent may be carried out by any process which is compatible with the properties of the agent used. thus the halogenating agent can be used in the gaseous state, pure or mixed with an inert gas; in the liquid state, pure or diluted with an inert liquid; in the dissolved state; in the solid state, by solid/solid reaction; or by the evolution of a volatile halogenated compound.

The conditions of the reaction between the oxygenated organic compound and with the halogenating agent (concentration, temperature and duration principally) are selected so as to obtain a solid product in which the atomic ratio of halogen/divalent metal is greater than 1. This atomic ratio is preferably greater than 1.5 with best results obtained when it is greater than 1.8.

The reaction conditions depend generally on the reactivity of the organic oxygenated compound and the halogenating agent as well as the process by means of which the reaction is carried out. They may vary within a very wide range, but, the temperature is preferably selected between —100° and 200° C. and more particularly between −25° and 100° C, with best results obtained between —15° and 50° C. It has been found in fact that with temperatures that are comparatively high the catalytic activity falls very markedly.

The duration of the reaction is generally between 1 minute and 24 hours and preferably between 15 minutes and 4 hours.

The quantity of halogenating agent used must be at least equal to the quantity which is stoichiometrically necessary to obtain the desired halogen/divalent metal ratio. When it is used in a diluted form, its concentration must be determined according to its reactivity in each particular case and this can be readily determined by making a test run.

The reaction of the organic oxygenated compound with the halogenating agent is preferably carried out prior to the reaction with the derivative of a metal of Groups IVb, Vb and VIb of the Periodic Table. However, it is possible to carry out the two reactions simultaneously.

When the reaction with the halogenating agent is carried out prior to the reaction with the derivative of a metal of Groups IVb, Vb and VIb of the Periodic Table, the solid reaction product, after preferably being separated from the unused reagents, may be washed with an inert hydrocarbon solvent and dried, for example in vacuo. As inert hydrocarbon solvent one preferably uses aliphatic or cycloaliphatic hydrocarbons such as butane, pentane, hexane, heptane, cyclohexane, methylcyclohexane or mixtures thereof.

After the reaction with the halogenating agent, the solid product (herein called the "activated solid support") of this reaction is reacted with a derivative of a metal of Groups IVb, Vb and VIb of the Periodic Table so as to form the cocatalyst. The derivative is preferably chosen from among the compounds of titanium, zirconium, vanadium and chromium with the best results obtained with the derivatives of titanium.

As such derivative there can be used the halides, oxyhalides, alkoxyhalides, oxyalkoxides and alkoxides. When halogenated compounds are used, it is preferred to use brominated and chlorinated derivatives and when compounds are used containing alkoxide radicals they are preferably chosen from among those whose alkoxide radicals, whether straight or branched, contain 1 to 20 carbon atoms and more particularly 1 to 10 carbon atoms each. Examples of compounds which can be used are: $TiCl_4$, $TiBr_4$, $VCl_4$, $VOCl_3$, $VOBr_3$, $CrO_2Cl_2$, $Ti(OC_2H_5)_3Cl$, $Ti(OiC_3H_7)_3Cl$, $Ti(OC_2H_5)_2Cl_2$, $Ti(OiC_3H_7)Cl_3$, $Ti(OiC_4H_9)_4$, $Ti(OiC_3H_7)_3Cl$ and $VO(OiC_3H_7)_3$. The compound giving best results is $TiCl_4$.

The reaction with the derivative may be carried out by any process which is compatible with the physical form of the reagents. The derivative may be used in the form of gas or vapor, possibly diluted with an inert gas, in the liquid form or in the form of a solution. As solvent one generally should use an inert hydrocarbon solvent such as butane, pentane, hexane, heptane, cyclohexane, methylcyclohexane or mixtures thereof. A particularly convenient method consists in bringing the reaction product with the halogenating agent in suspension in the pure derivative, brought into and maintained in the liquid state. One may also carry out the reaction by washing the solid product with the derivative when the latter is liquid under the reaction conditions.

The temperature and the pressure at which the reaction is carried out are not critical. For reasons of convenience a temperature between 0° and 300° C., preferably between 20° and 150° C., can be utilized.

The reagents are maintained in the presence of one another for a period of time which is sufficient for there to be a chemical fixing of the derivative of the metal of Groups IVb, Vb and VIb of the Periodic Table. Generally speaking this fixing is achieved after about one hour.

As mentioned above, the reaction of the organic oxygenated compound with the halogenating agent may be carried out at the same time as the reaction with the derivative of a metal of Groups IVb, Vb and VIb of the Periodic Table. In this case the conditions of temperature, duration and concentration must be selected so as to be compatible with the two reactions. The halogenating agent and the transition metal derivative are selected from among those described above.

In this case also the efficacy of the reaction with the halogenating agent is assessed by means of the atomic ratio of halogen/divalent metal. In order to do this one carries out by way of comparison the reaction between the organic oxygenated compound and the transition metal derivative in the absence of the halogenating agent but under conditions which are strictly identical with those used in the real reaction. One determines the quantity of halogen present in the products of the real reaction and of the comparative test. By the difference one obtains the quantity of halogen fixed onto the cocatalyst because of the halogenating agent. It is this quantity which is used to calculate the atomic ratio of halogen/divalent metal.

After the reaction with the derivative, the cocatalyst is collected separately. It may then be subjected to a treatment of extraction by means of the derivative used for the reaction. After this it is generally washed with an inert hydrocarbon solvent such as butane, pentane, hexane, heptane, cyclohexane, methylcyclohexane or mixtures thereof. This washing makes it possible to eliminate any excess of reagents.

The elementary analysis of the cocatalyst after washing shows that there is in fact a chemical reaction between the derivative and the activated solid support (compound of the divalent metal which has undergone halogenation) because the cocatalyst contains more than 1 mg/g of metal of the Groups IVb, Vb and VIb and generally more than 10 mg/g.

The catalyst according to the present invention also comprises an organometallic compound of a metal of groups Ia, IIa, IIb, IIIa and IVa of the Periodic Table, such as the organic compounds of lithium, magnesium, zinc, aluminium or tin. The best results are obtained with alkyl aluminiums.

One may use totally alkylated compounds whose alkyl chains generally contain 1 to 20 and preferably 1 to 10 carbon atoms and are straight or branched, such as for example n-butyl lithium, diethyl magnesium, diethyl zinc, trimethyl aluminum, triethyl aluminum, triisobutyl aluminum, trioctyl aluminum, tridecyl aluminum and tetrabutyl tin.

Also suitable are alkyl metal hydrides in which the alkyl radicals also contain from 1 to 20 carbon atoms and preferably from 1 to 10 carbon atoms, such as diisobutyl aluminium hydride and trimethyl tin hydride, and the alkyl halides of metals in which the alkyl radicals also contain from 1 to 20 and preferably 1 to 10 carbon atoms, such as ethyl aluminum sesquichloride, diethyl aluminum chloride and diisobutyl aluminum chloride.

Finally, one may also use organoaluminum compounds obtained by reacting trialkyl aluminums or dialkyl aluminium hydrides whose radicals contain from 1 to 20 carbon atoms with diolefins containing 4 to 20 carbon atoms. Among these compounds are those which are generally known as isoprenyl aluminums:

The process of the invention is applied to the polymerization of olefins such as $\alpha$-olefins having a terminal unsaturation whose molecule contains 2 to 18 and preferably 2 to 6 carbon atoms, such as ethylene, propylene, butene-1, 4-methylpentene-1 and hexene-1. It is also applicable to the copolymerization of these olefins with one another as well as with diolefins preferably containing from 4 to 18 carbon atoms and as used herein the phrase "polymerization and copolymerization of $\alpha$-olefins" is intended to include copolymerization of $\alpha$-olefins with diolefins. These diolefins may be unconjugated aliphatic diolefins such as hexadiene-1,4, unconjugated monocyclic diolefins such as 4-vinylcyclohexene, 1,3-divinylcyclohexane, cycloheptadiene-1,4 or cyclooctadiene-1,5, alicyclic diolefins having an endocyclic bridge such as dicyclopentadiene or norbornadiene and conjugated aliphatic diolefins such as butadiene and isoprene.

The process of the invention is especially useful in the manufacture of homopolymers of ethylene and copolymers containing at least 90 moles percent and preferably 95 moles percent of ethylene.

The polymerization may be carried out according to any known process: in solution or in suspension in a hydrocarbon solvent or diluent or in the gaseous phase. For processes in solution or in suspension one uses solvents or diluents analogous to those used for the washing of the catalytic element: these are preferably aliphatic or cycloaliphatic hydrocarbons such as butane, pentane, hexane, heptane, cyclohexane, methylcyclohexane and mixtures thereof.

It is also possible to carry out the polymerization in the monomer or one of the monomers maintained in the liquid state.

The polymerization pressure is generally between atmospheric pressure and 100 kg/cm$^2$, preferably 50 kg/cm$^2$. The temperature is generally chosen between 20° and 120° C. and preferably between 60° and 100° C. The polymerization may be carried out continuously or discontinuously.

The organometallic compound and the cocatalyst may be added separately to the polymerization medium. It is also possible to bring them into contact at a temperature between —40° and 80° C., for a period which may range up to 2 hours, before introducing them into the polymerization reactor. One may also bring them into contact in several stages or add a part of the organometallic compound before the reactor or again add several different organometallic compounds.

The total quantity of organometallic compounds used is not critical; it is generally between 0.02 and 50 mmoles per dm$^3$ of solvent, diluent or volume of reactor and preferably between 0.2 and 5 mmoles/dm$^3$.

The quantity of cocatalyst used is determined according to the content of metal of Groups IVb, Vb and VIb in the support. This is usually chosen so that the concentration is between 0.001 and 2.5 and preferably between 0.01 and 0.25 m.g.at. of metal per dm$^3$ of solvent, diluent or reactor volume.

The ratio of the quantities of organometallic compound and cocatalyst is also not critical. It is generally chosen in such a way that the ratio of organometallic compound to metal of Groups IVb, Vb or VIb expressed in moles/g.at. is greater than 1 and preferably greater than 10.

The molecular weight of the polymers manufactured according to the process of the invention may be regulated by the addition to the polymerization medium of one or more agents for modifying the molecular weight, such as hydrogen, zinc or diethyl cadmium, alcohols or carbon dioxide.

The specific gravity of the homopolymers manuactured according to the process of the invention may also be regulated by the addition to the polymerization medium of an alkoxide of a metal of Groups IVb and Vb of the Periodic Table. Thus one can produce polyethylenes with specific gravities intermediate between those of polyethylenes manufactured by a high-pressure process and those of the classic high-density polyethylenes.

Among the alkoxides which are suitable for this regulation those of titanium and vanadium whose radicals contain 1 to 20 carbon atoms each are particularly useful. One may mention among these $Ti(OCH_3)_4$, $Ti(OC_2H_5)_4$, $Ti[OCH_2CH(CH_3)_2]_4$, $Ti(OC_8G_{17})_4$ and $Ti(OC_{16}H_{33})_4$.

The instant invention makes it possible to produce large quantities of polyolefins containing very low quantities of catalyst residues. Thus, in the homopolymerization of ethylene, the productivity expressed in g of polyethylene per g of cocatalyst is far in excess of 5000 and even exceeds values as high as 30,000. For this reason the content of catalytic residues in the polymers obtained is very low.

It is known that these residues are very troublesome because they cause the corrosion of the apparatus used for the polymers and the appearance of undesirable colorings in the finished product. This is the reason why the polymers manufactured according to most of the known processes have to be purified. The polymers manufactured according to the present invention no longer need to be purified. One thus does away with a very involved and most costly operation when finishing the polymer.

Furthermore, the process is characterized by a very high degree of flexibility: it makes it possible to manufacture both polymers with a low melt index which are suitable for extrusion and blow-molding as well as polymers with a high melt index which can be used for injection by means of an adaptation of the polymerization temperature and possibly the addition of an agent for modifying the molecular weight.

The invention will be further described in connection with the following examples which are set forth for purpose of illustration only and are not to be construed as limiting the cope thereof in any manner.

EXAMPLE 1

250 mls of dry hexane and 30 g of magnesium methylate are added to a glass reactor with a 500 ml. capacity. The reactor is maintained under an atmosphere of nitrogen at a temperature of 0° C. and it is provided at its base with a plate of sintered glass through which a stream of gaseous hydrogen chloride is passed at 0° C. The rate of flow of this stream is 15 liters/hr. The temperature of the reactor is maintained at 0° C.

After 150 minutes the stream of hydrogen chloride is stopped and the liquid phase evacuated through the bottom of the reactor leaving the solid product of the reaction of $Mg(OCH_3)_2$ and HCL. The solid product is washed 10 times with dry hexane at 0° C. and is then dried in vacuo still at 0° C. The elementary analysis of the product shows that it contains 138 mg/g of magnesium and 396 mg/g of chlorine. The atomic ratio $Cl/M_g$ is therefore 1.97.

There is then introduced into the reactor 200 mls. of pure $TiCl_4$. The temperature is raised to about 130° C. and maintained under a reflux for 1 hour. The liquid phase is then evacuated through the bottom of the reactor and the solid product of the reaction is washed with dry hexane until all traces of chlorine in the washing solvent have disappeared. The product is then dried in vacuo. Elementary analysis of the cocatalyst shows that it contains 162 mg/g of magnesium, 634 mg/g of chlorine and 85 mg/g of titanium.

1 liter of hexane, 6.6 mg of the cocatalyst prepared and 200 mg of triisobutyl aluminum in the form of a 10% solution in hexane are added to a 3 liter capacity stainless steel polymerization reactor. The temperature of the reactor is then brought to 85° C. and ethylene is introduced under a pressure of 10 kg/cm$^2$ and hydrogen under a pressure of 4 kg/cm$^2$. The total pressure is maintained constant by the continuous addition of ethylene.

After polymerization has proceeded for 1 hour, the gas is released from the reactor and the polymer is collected and dried.

There is obtained 225 g of polyethylene corresponding to an hourly productivity of 34,000 g polyethylene per g of catalytic element and at a specific activity of 40,500 g polyethylene/hour.g.Ti.kg/cm$^2$ $C_2H_4$.

EXAMPLE 2

The preparation of the cocatalyst is carried out as described in Example 1 except that the gaseous hydrogen chloride is diluted with dry nitrogen. The mixture contains $\frac{1}{3}$ of HCl to $\frac{2}{3}$ of $N_2$.

The product of the reaction of $Mg(OCh_3)_2$ and HCl contains 99 mg/g of magnesium and 280 mg/g of chlorine. The atomic ratio of Cl/Mg is therefore 1.94.

The cocatalyst contains 172 mg/g of magnesium, 645 mg/g of chlorine and 71 mg/g of titanium.

After polymerization under the same conditions as set forth in Example 1 but by using 5.1 mg of cocatalyst, one obtains 107 g of polyethylene with a melt index of 0.39 g/10 mins. (measured according to ASTM STANDARD D 1238-57 T). The hourly productivity is therefore 21,000 g polyethylene/g catalytic element and the specific activity is 30,000 g polyethylene/hr.g.Ti kg/cm$^2$ $C_2H_4$.

EXAMPLE 3

The cocatalyst is prepared as in Example 1 except that one uses magnesium ethylate.

The product of the reaction between $Mg(OC_2H_5)_2$ and HCl contains 128 mg of magnesium and 363 mg of chlorine. The atomic ratio of Cl/Mg is therefore 1.95.

The cocatalyst contains 185 mg/g of magnesium, 677 mg/g of chlorine and 62 mg/g of titanium.

Polymerization is carried out as in Example 1 except that 5 mg of cocatalyst are used.

One obtains 180 g of polyethylene possessing a melt index of 0.69 g/10 mins. The hourly productivity is therefore 36,000 g polyethylene/g catalytic element and the specific activity is therefore 58,000 g polyethylene/hr.g.Ti kg/cm$^2$ $C_2H_4$.

EXAMPLE 4

Into a one-liter flask equipped with a reflux column and maintained under an atmosphere of nitrogen there is introduced 200 mls. of dry hexane, 21.7 g of magnesium ethylate and 113 g of thionyl chloride. It is heated under a reflux (at approximately 80° C.) for 3 hours and the reaction product (activated solid support) is collected and washed 10 times with dry hexane at 40° C. It is then dried in vacuo at 50° C. until the weight is constant.

The product of the reaction of $Mg(OC_2H_5)_2$ with $SOCl_2$ contains 142 mg/g of magnesium and 419 mg/g of chlorine. The atomic ratio of Cl/Mg is therefore 2.02.

The reaction product and 200 mls. of pure $TiCl_4$ are then introduced into a 1-liter flask equipped with a reflux column. It is heated under a reflux (approximately 130° C.) for 1 hour. The reaction product is then separated and it is washed with dry hexane until any trace of chlorine in the washing solvent has disappeared. It is then dried in vacuo.

the cocatalyst thus obtained contains 167 mg/g of magnesium, 698 mg/g of chlorine and 88 mg/g of titanium.

Polymerization is then carried as in Example 1, except there is used 20.5 mg of cocatalyst, the pressure of ethylene is 1 kg/cm$^2$, the pressure of hydrogen is 1 kg/cm$^2$ also and the temperature is maintained at 30° C.

One obtains 33 g of polyethylene. The hourly productivity is therefore 380 g polyethylene/g catalytic element and the specific activity is 18,000 g polyethylene/hr.g.Ti. kg/cm$^2$ $C_2H_4$.

EXAMPLE 5

The cocatalyst is prepared as in Example 4, except that one uses magnesium phenate.

The product of the reaction of $Mg(OC_6H_5)_2$ and $SOCl_2$ contains 112 mg/g of magnesium and 409 mg/g of chlorine. The atomic ratio of Cl/Mg is therefore 2.46.

The catalytic support contains 117 mg/g of magnesium, 489 mg/g of chlorine and 57 mg/g of titanium.

The polymerization is then carried out as in Example 1, except that one uses 29.2 mg of cocatalyst.

One obtains 84 g of polyethylene possessing a melt index of 1.4 g/10 mins. The hourly productivity is therefore 2900 g polyethylene/g catalytic element and the specific activity is 5,000 g polyethylene/hour.g-.Ti.kg/cm$^2$ $C_2H_4$.

EXAMPLE 6

The cocatalyst is prepared as in Example 4 except that one uses magnesium acetate hydrated with 4 molecules of water.

The product of the reaction of $Mg(OOCCH_3)_2.4H_2O$ with $SOCl_2$ contains 237 mg of magnesium and 656 mg of chlorine. The atomic ratio of Cl/Mg is therefore 1.90.

The cocatalyst contains 230 mg/g of magnesium, 685 mg/g of chlorine and 16 mg/g of titanium.

The polymerization is carried out as in Example 1 except that one uses 24.3 mg of cocatalyst.

One obtains 130 g of polyethylene possessing a melt index of 0.29 g/10 mins. The hourly productivity is therefore 5400 g polyethylene/g catalytic element and the specific activity is 33,000 g polyethylene/hr.g-.Ti.kg/cm$^2$ $C_2H_4$.

EXAMPLE 7

25 g of magnesium ethylate is mixed dry with 29 g of ammonium chloride. The mixture is brought to 250° C. and maintained at this temperature for 5 hours.

The product of the reaction of $Mg(OC_2H_5)_2$ with $NH_4Cl$ contains 242 mg/g of magnesium and 714 mg/g of chlorine. The atomic ratio of Cl/Mg is therefore 2.02.

The preparation of the cocatalyst is then continued as in Example 1 and the cocatalyst contains 229 mg/g of magnesium, 718 mg/g of chlorine and 0.1 mg/g of titanium.

A polymerization experiment is then carried out as in Example 1, except that one uses 10 mg of cocatalyst. One only collects 1 g of polyethylene.

This test shows that when the reaction of the organic oxygenated compound of a divalent metal with a halogenating agent is carried out at high temperature, the cocatalyst is not very active for polymerization.

EXAMPLE 8

Into a 1—liter flask under an atmosphere of dry nitrogen one introduces 250 mls. of trichloroethylene, 14 g of magnesium ethylate and 27 g of aluminum chloride, adding it very slowly. It is then heated under a reflux (approximately 87° C) for 30 minutes. The reaction product is filtered, washed with boiling trichlorethylene (5 times) and then with dry hexane (5 times) and dried in vacuo.

The product of the reaction of $Mg(OC_2H_5)_2$ with $AlCl_3$ contains 214 mg/g of magnesium and 554 mg/g of chlorine. The atomic ratio of Cl/Mg is therefore 1.77.

The preparation of the cocatalyst is completed as in Example 1. It contains 215 mg/g of magnesium, 708 mg/g of chlorine and 31 mg/g of titanium.

Polymerization is carried out as set forth in Example 1, except that one uses 4 mg of catalytic support. There is obtained 54 g of polyethylene possessing a melt index of 1 g/10 mins. The hourly productivity is therefore 13,500 g polyethylene/g catalytic element and the specific activity is 43,000 g polyethylene/hr.g-.Ti.kg/cm$^2$C$_2$H$_4$.

EXAMPLE 9

The cocatalyst is prepared as in Example 1 except that one uses anhydrous magnesium acetate, that the reaction is carried out with hydrogen chloride at 50° C., that this reaction is stopped after 90 minutes and the washings and drying are also carried out at 50° C.

The product of the reaction of $Mg(OOCCH_3)_2$ with HCl contains 132 mg/g of magnesium and 290 mg/g of chlorine. The atomic ratio of Cl/Mg is therefore 1.50.

the cocatalyst contains 171 mg/g of magnesium, 426 mg/g of chlorine and 30 mg/g of titanium.

After polymerization under the same conditions as in Example 1, one only obtains 7 g of polyethylene, whereas 22 mg of catalytic element have been used.

EXAMPLE 10

The preparation of a cocatalyst is carried out as in Example 1 except that one uses magnesium ethylate and one uses gaseous chlorine as the halogenating agent.

The product of the reaction of $Mg(OC_2H_5)_2$ with $Cl_2$ contains 146 mg/g of magnesium and 349 mg/g of chlorine. The atomic ratio of Cl/Mg is therefore 1.63.

The cocatalyst contains 194 mg/g of magnesium, 626 mg/g of chlorine and 49 mg/g of titanium.

The polymerization is carried out as in Example 1, except that one uses 6.4 mg of support.

One obtains 135 g of polyethylene possessing a melt index of 0.65 g/10 mins. The hourly productivity is therefore 21,000 g polyethylene/g catalytic element and the specific activity is 30,000 g polyethylene/hr.g-.Ti.kg/cm$^2$ C$_2$H$_4$.

EXAMPLE 11

The preparation of a cocatalyst is carried out as in Example 1 except that one uses magnesium phenate.

The product of the reaction of $Mg(OC_6H_5)$ and HCl contains 81 mg/g of magnesium and 226 mg/g of chlorine. The atomic ratio of Cl/Mg is therefore 1.92.

The cocatalyst contains 124 mg/g of magnesium, 553 mg/g of chlorine and 75 mg/g of titanium.

After polymerization under the same conditions as in Example 1 but using only 2.9 mg of cocatalyst, one obtains 107 g of polyethylene. The hourly productivity is 61,000 g polyethylene/g catalytic element. The specific activity is 78,000 g polyethylene/hr.g.Ti.kg/cm$^2$ C$_2$ H$_4$.

EXAMPLES 12 to 15

A cocatalyst prepared in accordance with the procedure set forth in Example 11 is used in a series of polymerization tests in which various organometallic compounds of aluminium are used. These tests are carried out under the same conditions as in Example 1 except that the pressures of ethylene and hydrogen are 5 and 2 kg/cm$^2$ respectively. The characteristics and the results of these tests are shown in Table A.

TABLE A

| Example No. | 12 | 13 | 14 | 15 |
|---|---|---|---|---|
| Quantity of cocatalyst, mg. | 8 | 9 | 7 | 8 |
| Nature of organometallic compound | $Al(CH_3)_3$ | $Al(C_8H_{17})_3$ | $Al(C_2H_5)_2Cl$ | isoprenyl aluminium |
| Quantity of organometallic compound, mg. | 80 | 366 | 140 | 148 |
| Weight of polyethylene obtained, g. | 117 | 130 | 89 | 109 |
| Melt index, g/10 mins. | 4.79 | 5.83 | 0.09 | 3.89 |
| Hourly productivity g polyethylene/g catalytic element | 14,500 | 14,500 | 12,500 | 13,500 |
| Specific activity g polyethylene/hr.g.Ti.kg/cm$^2$ C$_2$H$_4$ | 39,000 | 39,000 | 34,000 | 36,000 |

The isoprenyl aluminum used in Example 15 is the product of the reaction of triisobutyl aluminum with isoprene. It is characterized by the fact that the ratio of the hydrolysis products containing 5 carbon atoms to those containing 4 is 1.4.

EXAMPLE 16

One proceeds as in Example 11 except that the activated solid support is formed by the reaction between $Mg(OC_6H_5)_2$ and HCl is carried out at 25° C. The product of this reaction contains 93 mg/g of magnesium and 216 mg/g of chlorine. The atomic ratio of Cl/Mg is therefore 1.56.

The cocatalyst obtained contains 111 mg/g of magnesium, 509 mg/g of chlorine and 109 mg/g of titanium.

The polymerization is carried out as in Example 1, except that the pressure of ethylene is 5 kg/cm$^2$, the pressure of hydrogen is 2 kg/cm$^2$, the quantity of triisobutyl aluminum used is 100 mg and the quantity of catalytic element used is 8 mg.

One recovers 124 g of polyethylene. The hourly productivity is 15,500 g polyethylene g catalytic element and the specific activity is 25,000 g polyethylene/hr.g-.Ti.kg/$cm^2$ $C_2H_4$.

EXAMPLE 17

One reacts 12 g of magnesium ethylate with 40 g of aluminum chloride under conditions identical to those of Example 8. The product of this reaction contains 223 mg/g of magnesium and 696 mg/g of chlorine. The atomic ratio of Cl/Mg is therefore 2.14.

One completes the preparation of the cocatalyst as in Example 1 except that $TiCl_4$ is replaced by $VOCl_3$. The cocatalyst obtained contains 201 mg/g of magnesium, 663 mg/g of chlorine and 44 mg/g of vanadium.

The polymerization is carried out as in Example 1 except that one uses 75 mg of catalytic element. One obtains 20 g of polyethylene possessing a melt index of 2.67 g/10 mins. The hourly productivity is therefore 270 g polyethylene/g catalytic element and the specific activity is 600 g polyethylene/hr.g. V. kg/$cm^2$ $C_2H_4$.

EXAMPLE 18

A cocatalyst is prepared as in Example 17except that $VOCl_3$ is replaced by $Ti(OC_4H_9)_2Cl_2$. It contains 207 mg/g of magnesium, 625 mg/g of chlorine and 31 mg/g of titanium.

The polymerization is carried out as in Example 1 except that one uses 6 mg of cocatalyst. One obtains 82 g of polyethylene with a melt index equal to 1.15 g/10 mins. The hourly productivity is 13,500 g polyethylene/g catalytic element and the specific activity is 44,000 g polyethylene/hr.g.Ti.kg/$cm^2$ $C_2H_4$.

It will be understood that it is intended to cover all changes and modifications of the examples of the invention herein chosen for the purpose of illustration which do not constitute departures from the spirit and scope of the invention.

What is claimed is:

1. Catalysts for the polymerization and copolymerization of $\alpha$-olefins comprising an organometallic compound of a metal of Groups Ia, IIa, IIb, IIIa, and IVa of the Periodic Table and a solid cocatalyst comprising the reaction product of hydrogen chloride, with a solid organic oxygenated compound selected from a phenate or an alkoxide having A $C_1$–$C_{20}$ carbon atom radical attached, via oxygen, to magnesium, and reacting the reaction product with a compound of a transition metal selected from halides, oxyhalides, alkoxyhalides, oxyalkoxyhalides and alkoxides of titanium, the hydrogen chloride and organic oxygenated compound being in proportions required to result in a solid reaction product thereof having an atomic ratio of chlorine/magnesium from greater than 1.5 to 1.97 and contacted at a temperature of from $-15°$ to $+50°$ C.

2. A cocatalyst for use with an organometallic compound of a metal of Groups Ia, IIa, IIIa and IVa of the Periodic Table to catalyze the polymerization and copolymerization of $\alpha$-olefins comprising the reaction product of hydrogen chloride, with a solid organic oxygenated compound selected from a phenate or alkoxide having $C_1$–$C_{20}$ carbon atom radical attached, via oxygen, to magnesium, and reacting said reaction product with a compound of a transition metal selected from halides, oxyhalides, alkoxyhalides, oxyalkoxyhalides and alkoxides of titanium, the hydrogen chloride and organic oxygenated compound being in proportions required to result in a solid reaction product thereof having an atomic ratio of chloride/magnesium from greater than 1.5 to 1.97 and reacted at a temperature of from $-15°$ to $+50°$ C.

3. A method for making the cocatalyst of claim 2 comprising the steps of reacting the hydrogen chloride with the organic oxygenating compound in an amount sufficient to obtain the chloride/ magnesium metal atomic ratio from greater than 1.5 to 1.97 at a temperature of —15° to +50° C. for a time sufficient to form a solid reaction product and reacting said solid reaction product with a derivative of titanium metal at a temperature and for a time sufficient to chemically fix the titanium metal derivative to the solid reaction product.

4. A process for the polymerization of $\alpha$-olefins which comprises contacting the $\alpha$-olefin at a temperature and at a pressure sufficient to initiate the reaction, with a catalytic amount of a catalyst comprising an organometallic compound of a metal of Groups Ia, IIa, IIb, IIIa, IVa of the Periodic Table and a solid cocatalyst comprising the reaction product of hydrogen chloride, with a solid organic oxygenated compound selected from a phenate or alkoxide having a $C_1$–$C_{20}$ carbon radical attached, via oxygen, to magnesium, and reacting the reaction product with a derivative of a transition metal selected from halides, oxyhalides, alkoxyhalides, oxyalkoxyhalides and alkoxides of titanium, the hydrogen chloride and organic oxygenating compound being in proportions required to result in a solid reaction product thereof having an atomic ratio of chlorine/magnesium of from greater than 1.5 to 1.97 and reacted at a temperature of from $-15°$ to $+50°$ C.

* * * * *

UNITED STATES PATENT AND TRADEMARK OFFICE

CERTIFICATE OF CORRECTION

PATENT NO. : 4,144,390

DATED : March 13, 1979

INVENTOR(S) : Jean-Louis Derroitte; Andre Delbouille

It is certified that error appears in the above-identified patent and that said Letters Patent are hereby corrected as shown below:

Column 6, line 44, "cope" should read -- scope --.

Column 7, line 29, "$Mg(OCh_3)_2$" should read -- $Mg(OCH_3)_2$ --.

Column 8, line 11, "the" should read -- The --.

Column 9, line 42, "the" should read -- The --.

Column 10, line 1, "$Mg(OC_6H_5)$" should read -- $Mg(OC_6H_5)_2$ --.

Signed and Sealed this

*Twenty-fourth* Day of *July 1979*

[SEAL]

*Attest:*

LUTRELLE F. PARKER

*Attesting Officer* *Acting Commissioner of Patents and Trademarks*